(12) United States Patent
van der Linden

(10) Patent No.: US 6,494,858 B1
(45) Date of Patent: Dec. 17, 2002

(54) METHOD AND A DEVICE FOR PRODUCING AN ATMOSPHERE IN A REGION, AND USE OF CARBON DIOXIDE FOR THE MANUFACTURE OF A MEDICAMENT

(75) Inventor: Jan van der Linden, Saltsjöbaden (SE)

(73) Assignee: Cardia Innovation AB, Stockholm (SE)

( * ) Notice: Subject to any disclaimer, the term of this patent is extended or adjusted under 35 U.S.C. 154(b) by 0 days.

(21) Appl. No.: 09/554,461

(22) PCT Filed: Nov. 20, 1998

(86) PCT No.: PCT/SE98/02115

§ 371 (c)(1),
(2), (4) Date: Jun. 28, 2000

(87) PCT Pub. No.: WO99/29249

PCT Pub. Date: Jun. 17, 1999

(30) Foreign Application Priority Data

Nov. 20, 1997 (SE) .................................................. 970461

(51) Int. Cl.[7] .............................................. A61B 17/00
(52) U.S. Cl. ........................... 604/23; 128/847; 128/897
(58) Field of Search ..................... 604/23, 24; 128/846, 128/847, 856, 897

(56) References Cited

U.S. PATENT DOCUMENTS

| | | |
|---|---|---|
| 3,692,024 A | 9/1972 | Von Otto |
| 3,982,533 A | 9/1976 | West |
| 4,275,719 A | 6/1981 | Mayer |
| 4,422,369 A | 12/1983 | Smets |
| 5,849,005 A | * 12/1998 | Garrison et al. .............. 604/26 |

FOREIGN PATENT DOCUMENTS

| | | |
|---|---|---|
| DE | 2646710 | 4/1978 |
| DE | 2040047 | 3/1979 |
| DE | 2903842 | 7/1980 |
| FR | 2656218 | 6/1991 |
| SE | 401783 | 5/1978 |
| WO | WO9639942 | 12/1996 |
| WO | WO9726034 | 7/1997 |

* cited by examiner

Primary Examiner—J. Casimer Jacyna
(74) Attorney, Agent, or Firm—Greer, Burns & Crain, Ltd.

(57) ABSTRACT

A method for creating an atmosphere in an area which adjoins an outwardly open, inner portion of a body of a human being or an animal, where the portion is uncovered and has direct contact with a surrounding atmosphere, the method including the steps of supplying a gas to the area, wherein the gas forms a main component in the atmosphere and includes a substantial amount of carbon dioxide. The gas is supplied to the area in a substantially laminar, substantially continuous flow and in such manner that the gas forces air away from the open portion and prevents air from penetrating the area of the open portion. The atmosphere prevents growth of microorganisms including bacteria and viruses in the area.

10 Claims, 3 Drawing Sheets

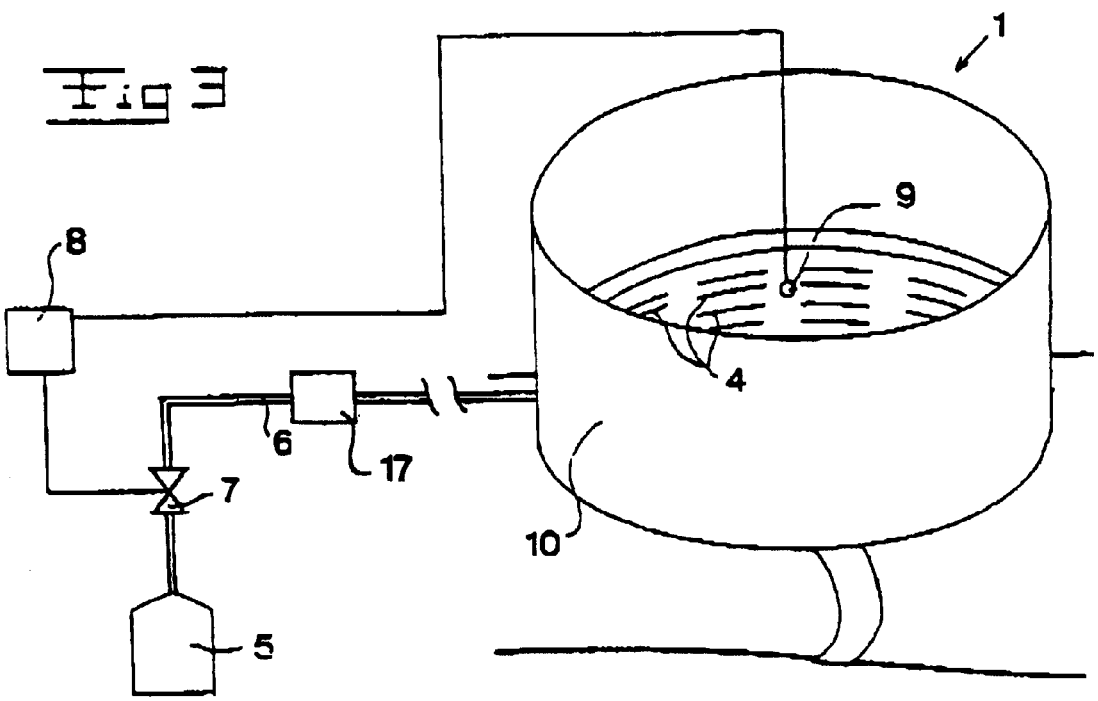
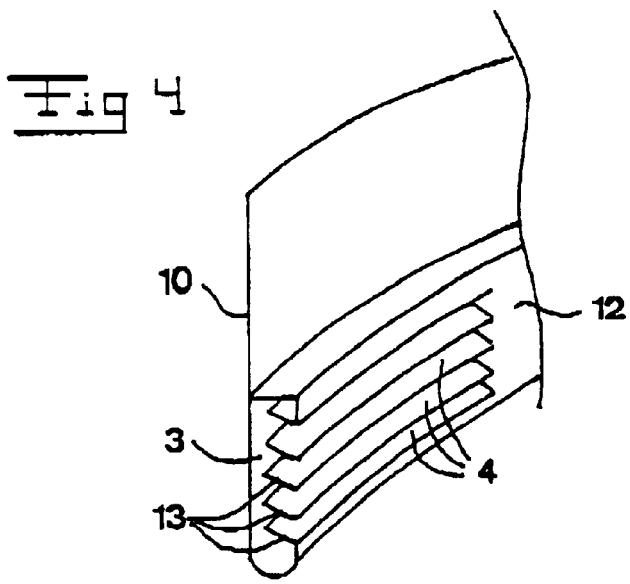

METHOD AND A DEVICE FOR PRODUCING AN ATMOSPHERE IN A REGION, AND USE OF CARBON DIOXIDE FOR THE MANUFACTURE OF A MEDICAMENT

THE BACKGROUND OF THE INVENTION AND PRIOR ART

The present invention refers to a method for creating an atmosphere in an area which adjoins an outwardly open, inner portion of the body of a human being or an animal, comprising the step of supplying a gas to the area which gas forms a main component in said atmosphere. The invention also refers to a device for creating an atmosphere in an area which adjoins an outwardly open, inner portion of the body of a human being or an animal, which device comprises a gas supply member which is connectable to a gas source.

When an outwardly open portion arises on the body of a human being or an animal, the risk for infections due to bacteria or any other micro-organisms increases, which micro-organisms may easily penetrate the body because the protective skin is removed. Such open portions arise in connection with operations and other surgery operations and in the case of open wounds, which may have been caused by different injuries, accidents or diseases. In order to reduce this risk of infection one attempts, at least at hospitals, to keep the surrounding atmosphere and the skin as sterile as possible by filtering and cleaning, respectively, and by the use of different types of disinfectant. Of course it is important to close as quick as possible such open portions to prevent the penetration of bacteria.

Furthermore, in connection with operations tissues and vessels are exposed to air, the main components of which, i.e. nitrogen and oxygen, hardly dissolve in tissue. This results in an activation of a plurality of so-called cascade systems, inter alia within coagulation. Within vessel and heart surgery, the situation is more complicated by the fact that due to the opening of the vessels and the heart one can both actively and passively introduce air into the cavities of the vessels and the heart. Thereafter, it is very difficult to remove completely the air from the vessels and the heart merely by blood filling without air bubbles being further transported with the bloodstream, due to the fact that air mixed with blood gives bubbles similar to a foam. When the bubbles of air are transported with the bloodstream to the capillaries, the bubbles remain in the capillaries during some minutes, whereafter they are slowly absorbed or slowly pass the capillaries. The inside of the vessels, including the inside of the capillaries, is covered with endothelial, which is very depending on oxygen, i.e. depending on the oxygen bond in the blood, and a remaining air bubble in a small vessel or capillary results in an endothelium injury. Also when the bubble has been absorbed or transported further this activates and results in the injured endothelium wall being covered by white blood cells which in turn already can be ready to attach to the injured endothelium due to the so called operation trauma and/or the exposing to foreign material through for example the use of a heart-lung-machine. The result is an embolisation, i.e. a blocking of the vessel and the capillary of firstly the air bubble, which remains in the vessel during in the range of minutes, and secondly of white blood cells, which remain during a long time because of the following reaction between the injured endothelium and active white blood cells. Thereby, the area which is supported by the vessel and the capillary gets no blood support, whereby in particular oxygen depending tissue, especially the brain, is injured.

SUMMARY OF THE INVENTION

The object of the present invention is to create a desired atmosphere in connection with outwardly open body portions, such as in connection with surgery operations. In particular, according to a first aspect of the invention, it is aimed at the prevention of bacteria growth in such portions and according to a second aspect of the invention, it is aimed at a reduction of the problem of embolisation in connection with surgery operations, in particular vessel and heart surgery.

This object is obtained by the device initially defined and characterized in that said gas comprises a substantial amount of carbon dioxide.

Carbon dioxide has bacteriostatic/bactericidal properties and by creating an atmosphere of carbon dioxide in an area, which surrounds an open portion of the body, one may effectively prevent a bacterial growth in the open portion, for example a wound or a surgical cut. Moreover, the supplied carbon dioxide may be substantially completely sterile, i.e. the supplied gas comprises no micro-organisms or bacteria, and in this way bacteria or micro-organisms which exist in the surrounding air are prevented from reaching said area. The bacteria or micro-organisms which exist in the area or which for some reason would manage to penetrate the area can however not propagate themselves. Furthermore, one may by the supply of the carbon dioxide gas prevent the entrance of the surrounding air to an open area of the body in connection with an operation or a surgery operation. Consequently, air may not penetrate the bloodstream and cause the above discussed air embolisation. Carbon dioxide, which in relation to the main components in air, i.e. oxygen and nitrogen, has a high solubility in tissue, may be permitted to penetrate the open body portion because carbon dioxide is not going to create bubbles but rapidly be resorbed in the tissue and in this way embolisation and thereby blocking of small vessels and capillaries, may be avoided. Consequently, the carbon dioxide does not remain as bubbles in the blood vessels and will therefore not prevent the bloodstream in the same way as common air. Moreover, carbon dioxide is more heavy than air and therefore one may in a simple way create an atmosphere free from air in said area, since the more heavy carbon dioxide will pass downwardly into the open body portion and force away the air which exists down in this open portion. Furthermore, the carbon dioxide is substantially inert with regard to living organisms at least when it appears in moderate quantities.

According to a further embodiment of the invention, said gas is supplied to the area in a substantially continuous flow. In this way, it is possible to guarantee an atmosphere which is free from air in said area although some of the supplied gas leaves the area.

According to a further embodiment of the invention, said gas is supplied to the area in a substantially laminar flow. By such a laminar flow, it is possible to supply said gas in a controlled way and thereby it is also possible to avoid or at least substantially reduce the presence of turbulence in the area, which otherwise might result in the suction of air from the surrounding atmosphere into the area.

According to a further embodiment of the invention, the area is shielded off from the surrounding atmosphere in such a way that the supplied gas is kept within the area. By such a shielding off, the surrounding air is also prevented from penetrating the area, and consequently the maintaining of the atmosphere free from air is facilitated.

According to a further embodiment of the invention, a stream of said gas is supplied in a direction towards a part of said inner body portion. At least in some cases such a simple performing of the method, with only one or a few flow streams of said gas, is enough for keeping, within a limited area, the atmosphere substantially free from air.

According to a further embodiment of the invention, said gas is humidified before it is supplied to the area. In such a way, one may in an effective way reduce the evaporation from the open portion and consequently prevent dehydration.

The object is also obtained by the device initially defined and characterized by a gas source which comprises a gas with a substantial amount carbon dioxide and in that the gas supply member is arranged to supply said gas to said area in such a way that the carbon dioxide forms a main component in said atmosphere.

According to embodiments of the instant invention, the gas supply member may permit the supply of the gas to the area in a substantially continuous flow. The gas supply member may also comprise a nozzle which is arranged to supply the gas in a substantially laminar flow to the area. The gas supply member may further include a shield member, which is provided to be arranged around the area and to prevent the supplied gas from exiting the area. Further, the gas supply member may include several nozzle openings, which are arranged to direct a flow of the gas towards the center of the area. Also, the gas supply member may be configured so that nozzle openings are provided in a ring-shaped configuration, which is arranged to surround the area.

The object is also obtained by a use of carbon dioxide for the manufacture of a medicament to be supplied to an outwardly open inner portion of the body of a human being or an animal in order to create an atmosphere, which prevents growth of micro-organisms comprising bacteria and virus in said area. Furthermore, the object is obtained by a use of carbon dioxide for the manufacture of a medicament to be supplied to an outwardly open inner portion of the body of a human being or an animal in order to create an atmosphere, which prevents penetration of air into said area.

BRIEF DESCRIPTION OF THE DRAWINGS

The present invention is now to be explained more closely by means of an embodiment and with reference to the attached drawings, in which FIG. 1 discloses a schematic view of a device according to a first embodiment of the invention.

FIG. 3 discloses a schematic view of a device according to a second embodiment of the invention.

FIG. 4 discloses a cross-sectional view through a part of the device in FIG. 2.

DETAILED DESCRIPTION OF DIFFERENT EMBODIMENTS OF THE INVENTION

Figure 1:
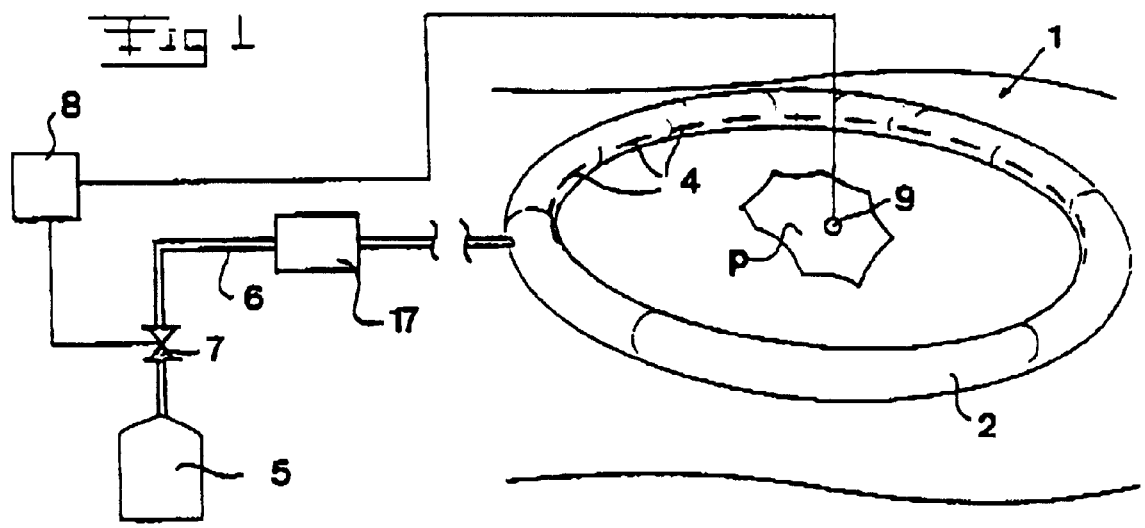
Figure 2:
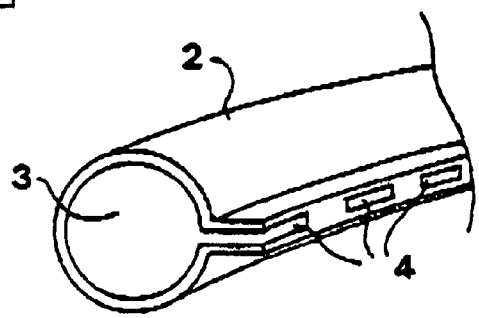
FIG. 2 discloses a cross-sectional view through one part of the device in FIG. 1.

With reference to FIGS. 1 and 2, a device is shown for supplying a gas to an area which surrounds and adjoins an open, inner portion of a human being, which portion is open at least during a limited time period. Such an open portion is formed in connection with surgery operations. In connection with, for example, heart operations a substantial part of the inside of the thorax is uncovered so that this part in normal cases has direct contact with the surrounding atmosphere, i.e. with air and consequently it is exposed to attack from the bacteria and micro-organisms which exist in the environment.

The device comprises a gas supply member 1 which is designed as a hose-like, tubular body 2, which extends in a wholly or partially closed ring and is intended to be arranged around an open portion P of a patient who is subjected to a surgery operation. The tubular body 2 forms an annular channel 3 and comprises a number of openings 4, which face the centre of the ring and which form nozzles for outflowing gas. The annular channel 3 is connected to a gas source in the shape of a gas container 5 through a gas conduit 6. Consequently, gas from the gas container 5 may be supplied to the annular channel 3 through the gas conduit 6 and be blown out towards the centre of the gas supply member 1 through the openings 4. The gas conduit 6 comprises a valve member 7 by which the gas supply to the annular channel 3 is adjustable. In the example shown, the valve member 7 is controlled with the aid of a control member 8 connected to the valve member 7. The control member 8 may in turn be connected to a gas-sensing member 9, which is arranged to sense the concentration of the supplied gas or of the air in the area in question. With the aid of such a sensing, the gas supplied to the area may be controlled in, for example, such a way that if an increased air concentration is determined, the gas supplied is also increased or if the concentration of air in the area exceeds a predetermined level, the gas supply is increased.

The openings 4 are in the example disclosed in FIG. 1 designed as slit-shaped openings 4, which extend in the direction of the circumference of the body 2. Also other shapes of the openings 4 are possible, for example they may be formed by substantially circular or oval apertures. FIG. 2 shows a part of the tubular body 2 and how the openings 4 may be shaped. Thereby, it is seen that the openings 4 have an extension also in the out-blow-direction of the gas and that the length of this extension exceeds the wall thickness of the hose-like body 2 forming the annular channel 3. Thereby, it is possible to direct the gas flow in a desired direction towards an open portion of the body of the patient. By this embodiment of the openings 4, it is also possible to achieve a substantially laminar gas flow. It is to be noted that within the scope of the invention, it is also possible to let simple apertures in the wall of the hose-like body 2 form the nozzles for the gas supply.

The gas supply member 1 may be produced from a number of different materials. However, it is advantageously produced from some flexible material, such as rubber or plastic. In this way, the gas supply member 1 may adjust itself to the contour of the body of the patient to whom it is placed. Since the hose-like, tubular body 2 forms a closed loop and abuts the body of the patient, it will also, at least to some extent, prevent the supplied gas from exiting the area, which the gas supply member 1 encloses.

With reference to FIGS. 3 and 4, a second embodiment of the gas supply member according to the invention is disclosed. It is to be noted here that components with substantially the same function have been provided with the same reference signs in the different embodiments disclosed. The second embodiment differs from the first embodiment with regard to the design of the gas supply member 1, which comprises a cylinder-shaped shield member 10, which is applied on the body of the patient and attached with the aid of a belt member 11 or the like, which extends around the patient. Furthermore, as is disclosed in FIG. 4, the gas supply member 1 comprises an annular channel 3, which is defined by a wall member 12, arranged at the inner side of the shield member 10. The wall member 12 comprises a number of elongated openings 4, which extend in the direction of the circumference of the shield member 10. Each opening 4 is defined by two lamella or guide vanes 13, which together with the openings 4 form a nozzle, by which the supplied gas may be directed in a desired direction towards an open portion of the body of the patient. With the aid of these lamella 13, it is also possible to achieve a substantially laminar gas flow. Also in this case, the gas supply member 1 may be produced from a number of different materials. Advantageously, at least the lower portion of the gas supply member 1, which abuts the patient, is produced from some flexible material, such as rubber or plastic. In this way, the gas supply member 1 may adapt itself to the contour of the body of the patient to whom it is attached. Due to the relatively high shield member 10, which may be applied in such a way that it extends upwardly from the body of the patient, the supplied gas will be prevented from exiting the area, which the gas supply member 1 encloses. It is to be noted that also in the second embodiment, the openings 4 can have many different shapes, such as for example a plurality of small round or oval apertures with or without lamella or guide vanes for guiding the gas flow.

Figure 5:
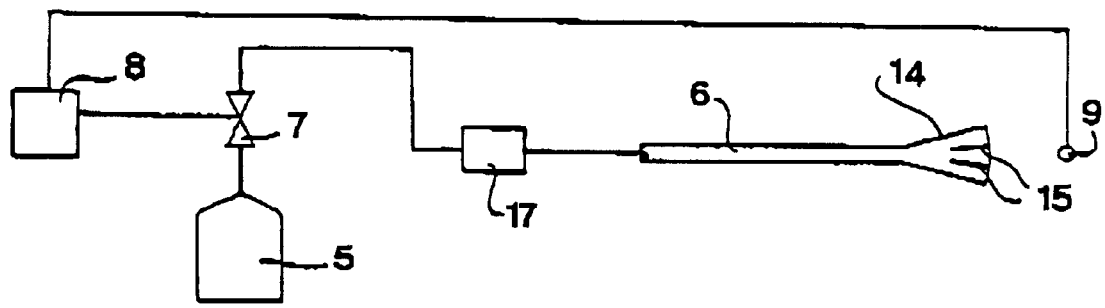
FIG. 5 discloses a schematic view of a device according to a third embodiment of the invention.

FIG. 5 discloses a third embodiment, wherein the gas supply member 1 only comprises a gas conduit 6 with a funnel-shaped, expansive nozzle 14. The nozzle 14 comprises, in the example disclosed, two guide vanes 15, which contribute to the possibility of directing the gas flow in a desired direction towards an open portion of the body of the patient. With the disclosed, expanding nozzle 14, it is also possible to achieve a substantially laminar gas flow.

Figure 6:
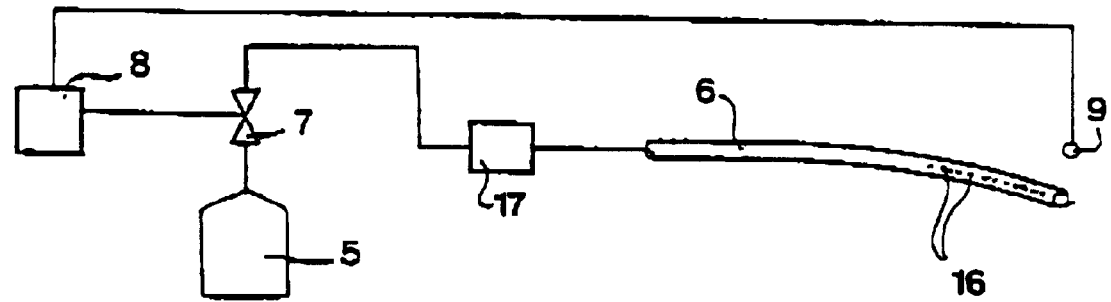
FIG. 6 discloses a schematic view of a device according to a fourth embodiment of the invention.

FIG. 6 discloses a fourth embodiment, which is similar to but less complicated than the third embodiment. In the fourth embodiment, the gas supply member comprises only a flexible hose 6, which is provided with a number of small apertures 16, through which the supplied gas is discharged. This embodiment is suitable in particular for application in cavities in the body of the patient.

The device may, but not necessarily, comprise a humidifying member 17, see FIGS. 1, 3, 5 and 6, by which the supplied gas may be humidified. The humidifying member 17 may be of a know type per see and provided to humidify the gas with water or water steam, for example a physiological sodium chloride solution.

According to a preferred embodiment of the invention, the supplied gas from the gas container 5 is mainly carbon dioxide, which has a high solubility in body tissue, which is substantially bacteriostatic or inert with regard to living organisms and which furthermore is heavier than air. The gas may be supplied by the aid of a pressure, above atmospheric, in the gas container 5 or by the aid of a pump (not disclosed). To maintain a laminar gas flow, the flow speed has to be relatively low.

It is also possible to cool the gas, which is supplied the open portion P to a temperature level, which is somewhat lower than the temperature of the surrounding air. Such a cooling may take place both if the gas is humidified and if it is not humidified. The cooling has the advantage that the supplied gas, due to its lower temperature, obtains a higher density and consequently becomes heavier. In such a way, the gas will easier penetrate the open portion P, and consequently, more easily force the air away. Furthermore, the carbon dioxide, which has a relatively low temperature, will further restrain a possible growth of bacteria or other micro-organisms. Such a cooling may be achieved in many different ways, for example with a heat exchanger, which is arranged in connection with the gas conduit 6.

The present invention is not limited to the above-disclosed embodiments but can be varied and be modified within the scope of the following patent claims. For example, it is to be noted that the channel 3 disclosed in FIGS. 1–not need to extend in a closed, annular loop but can extend along only a part of a round. It is also to be noted that it within the scope of the invention is possible to form a completely closed area around the open portion and that said gas is supplied to this enclosed atmosphere and the air is removed before, after or during the gas supply. The size of this area may be varied for different applications and it is also possible to let this area be big enough to include completely or partly the individuals performing the surgery operation within the area.

The defined outwardly open, inner portion in this present application may have an arbitrary size and comprises not only large operation fields but also smaller passages through the skin, for example smaller wounds. Consequently, the invention is also applicable to the case that a gas-formed medium is permitted to flow towards such a smaller passage in order to force away the blood, which flow out from the passage. In such a way, one may visualise the operation field and thereby facilitate the surgery operation at the same time as an atmosphere free from bacteria is created.

What is claimed is:

1. A method for creating an atmosphere in an area which adjoins an outwardly open, inner portion of a body of a human being or an animal, said portion being uncovered and having direct contact with a surrounding atmosphere, the method comprising the steps of:

supplying a gas to the area, wherein said gas forms a main component in said atmosphere and comprises a substantial amount of carbon dioxide;

supplying said gas to the area in a substantially laminar, substantially continuous flow and in such manner that said gas forces air away from the open portion and prevents air from penetrating the area of the open portion, and wherein said atmosphere prevents growth of micro-organisms comprising bacteria and virus in said area.

2. A method according to claim 1, wherein the area is shielded off from the surrounding atmosphere in such a way that the supplied gas is kept within the area.

3. A method according to claim 1, wherein a stream of said gas is supplied in a direction towards a part of said inner body portion.

4. A method according to claim 1, wherein said gas is humidified before it is supplied to the area.

5. A device which is provided to create an atmosphere in a area, which adjoins an outwardly open, inner portion of the body of a human being or an animal, said portion being uncovered and having direct contact with a surrounding atmosphere, which device comprises a gas supply member, which is connectable to a gas source comprising a gas with a substantial amount of carbon dioxide, wherein the gas supply member is arranged to supply said gas to said area in such a way that the carbon dioxide forms a main component in said atmosphere, wherein the gas supply member is arranged to enable the supply of said gas in a substantially continuous flow to the area, wherein the gas supply member is arranged to supply said gas to said area in such a way that said gas forces air away from the open portion and prevents air from penetrating the area of the open portion, and wherein the gas supply member comprises a nozzle, which is provided to supply said gas in a substantially laminar flow to the area.

6. A device according to claim 5, wherein it comprises a shield member, which is provided to be arranged around the area and to prevent the supplied gas from exiting the area.

7. A device according to claim 5, wherein t he gas supply member comprises several nozzle openings, which are arranged to direct a flow of said gas towards the center of the area.

8. A device according to claim 7, wherein the nozzle openings are provided in a ring-shaped configuration, which is arranged to surround the area.

9. A device according to claim 5, wherein the gas supply member comprises a nozzle, which is arranged to supply a stream of said gas and which is adjustable in a direction towards a part of said inner body portion.

10. A device according to claim 5, wherein a humidifying member is provided to humidify said gas.

* * * * *